United States Patent [19]
Brann

[11] Patent Number: 6,059,576
[45] Date of Patent: *May 9, 2000

[54] TRAINING AND SAFETY DEVICE, SYSTEM AND METHOD TO AID IN PROPER MOVEMENT DURING PHYSICAL ACTIVITY

[76] Inventor: Theodore L. Brann, P.O. Box 1897, Mission, Tex. 78572

[*] Notice: This patent issued on a continued prosecution application filed under 37 CFR 1.53(d), and is subject to the twenty year patent term provisions of 35 U.S.C. 154(a)(2).

[21] Appl. No.: 08/976,228

[22] Filed: Nov. 21, 1997

[51] Int. Cl.⁷ .............................. A63B 69/00; G09B 9/00
[52] U.S. Cl. ........................ 434/247; 128/782; 600/595; 601/34; 482/8; 482/901; 340/686.1; 702/101
[58] Field of Search ..................................... 434/118, 247, 434/365; 482/3, 4, 6, 8, 9, 92, 137, 900–903; 128/897, 905, 782; 600/301, 502, 587, 594, 595; 601/5, 33, 34; 73/379.01, 379.06, 379.08; 340/573.1, 573.7, 686.1, 689; 364/167.12; 702/19, 41, 101, 141, 174

[56] References Cited

U.S. PATENT DOCUMENTS

| | | |
|---|---|---|
| 4,571,682 | 2/1986 | Silverman et al. .................. 482/903 X |
| 4,665,928 | 5/1987 | Linial et al. . |
| 4,911,427 | 3/1990 | Matsumoto et al. ................ 482/902 X |
| 4,912,638 | 3/1990 | Pratt, jr. .............................. 482/903 X |
| 4,934,694 | 6/1990 | McIntosh ............................ 482/902 X |
| 5,042,505 | 8/1991 | Mayer et al. . |
| 5,052,375 | 10/1991 | Stark et al. .......................... 482/902 X |
| 5,128,655 | 7/1992 | Shore . |
| 5,348,519 | 9/1994 | Prince et al. ........................ 482/903 X |
| 5,373,858 | 12/1994 | Rose et al. . |
| 5,375,610 | 12/1994 | LaCourse et al. . |
| 5,394,888 | 3/1995 | Stone et al. . |
| 5,398,697 | 3/1995 | Spielman . |
| 5,435,321 | 7/1995 | McMillen et al. . |
| 5,462,065 | 10/1995 | Cusimano . |
| 5,469,862 | 11/1995 | Kovacevic . |
| 5,474,088 | 12/1995 | Zaharkin et al. . |
| 5,513,651 | 5/1996 | Cusimano et al. . |
| 5,588,444 | 12/1996 | Petragallo . |
| 5,621,667 | 4/1997 | Waters . |
| 5,715,160 | 2/1998 | Plotke ................................. 482/902 X |

Primary Examiner—Joe H. Cheng
Attorney, Agent, or Firm—Locke Liddell & Sapp LLP

[57] ABSTRACT

An electronic device, system and method to monitor and train an individual on proper motion during physical movement. The system employs an electronic device which tracks and monitors an individual's motion through the use of an accelerometer capable of measuring parameters associated with the individual's movement. The device also employs a user-programmable microprocessor which receives, interprets, stores and responds to data relating to the movement parameters based on customizable operation parameters, a real-time clock connected to the microprocessor, memory for storing the movement data, a power source, a port for downloading the data from the device to other computation or storage devices contained within the system, and various input and output components. The downloadable, self-contained device can be worn at various positions along the torso or appendages being monitored depending on the specific physical task being performed. The device also detects the speed of movements made while the device is being worn. When a preprogrammed recordable event is recognized, the device records the time and date of the occurrence while providing feedback to the wearer via visual, audible and/or tactile warnings.

29 Claims, 9 Drawing Sheets

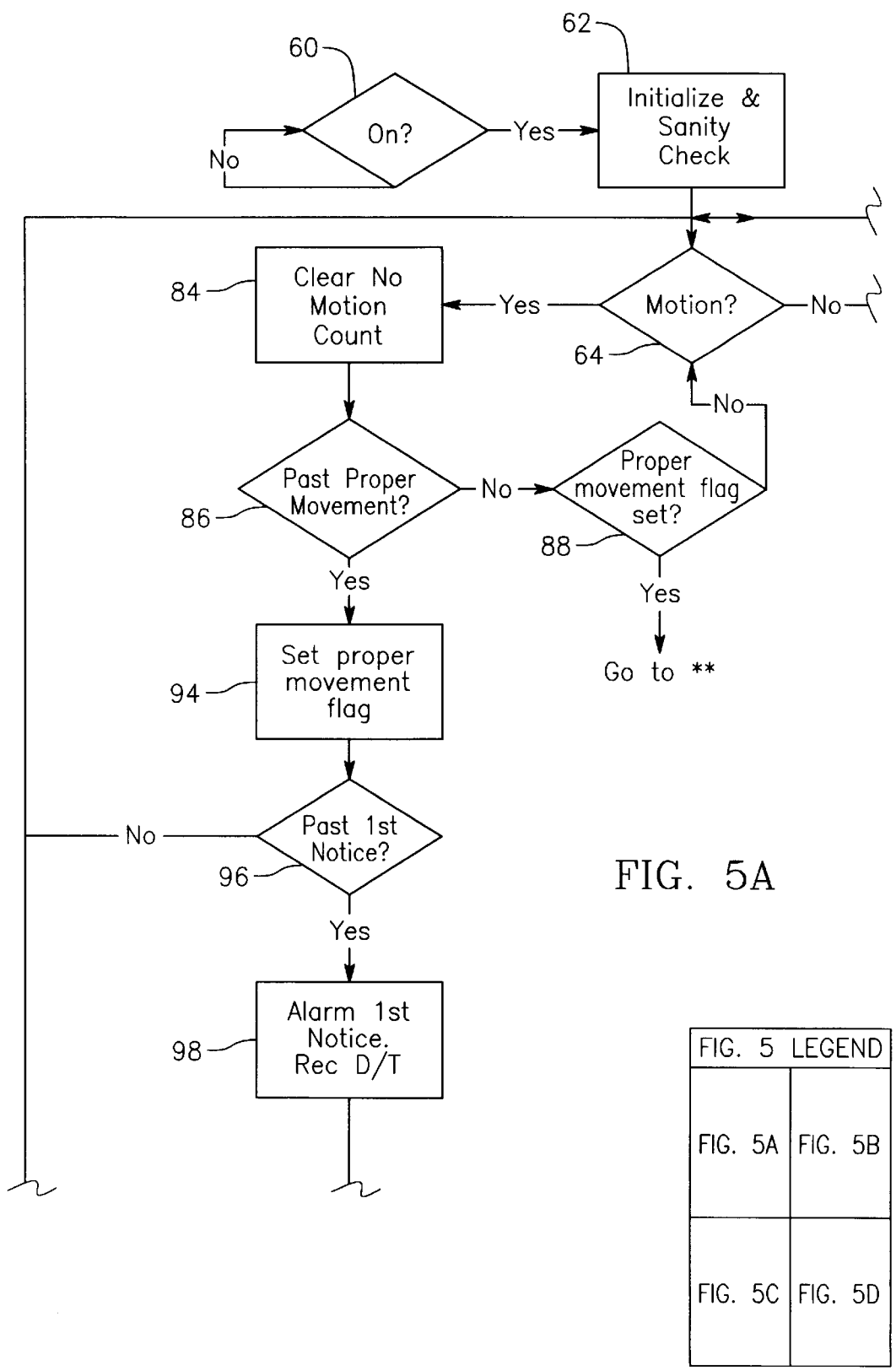

TRAINING AND SAFETY DEVICE, SYSTEM AND METHOD TO AID IN PROPER MOVEMENT DURING PHYSICAL ACTIVITY

FIELD OF THE INVENTION

This invention relates to the field of electronic training and safety devices used to monitor human physical activity. More specifically, the invention detects, measures, records, and/or analyzes the time, date, and other data associated with movement of the device and produces meaningful feedback regarding the measured movement.

BACKGROUND

It has long been known that improper physical movement, especially when repeated, can result in injury to a person. This injury may manifest itself in a wide range of symptoms anywhere from sore or bruised muscles to chronic, debilitating loss of movement. In order to study and better understand safe human movement which does not result in injury, a variety of sensing, monitoring, and notification devices have been created. In general, these devices fall under the general category of range of motion (ROM) detectors.

Several such inventions have been patented to measure the range of motion of various joints of the human body for both medical studies and industry applications. Typically, these inventions require that two people simultaneously use the device: the patient/wearer and the operator of the device. The purpose of these devices is to quantitatively determine a range of motion of a human joint in angular degrees as exemplified by U.S. Pat. Nos. 4,665,928; 5,042,505; and 5,373,858. Although the devices disclosed in these patents serve the purposes for which they are intended, they do not warn the device wearer when the wearer is nearing, or has reached, a potentially dangerous angle of movement.

Another class of ROM devices has attempted to provide a warning to the wearer through an audible alarm or flashing light. Typically, these devices activate the alarm when a predetermined angle of flexion or extension has been exceeded in order to try and reduce the number of injuries that can occur as a result of the improper movement. Because of the general weakness of the human spine and back muscles, most of these devices are geared toward detecting improper torso movement while lifting an object. One such invention described in U.S. Pat. No. 5,128,655 uses a mercury switch set at a predetermined angle to trigger a counting mechanism in order to count the number of times the predetermined angle is exceeded during forward bending. Another such device described in U.S. Pat. No. 5,398,697 uses a "T" shaped collimated light beam to detect both forward and lateral bending of the spine. However, these devices are not convenient to operate and serve to merely report rather than analyze the information detected.

Training an individual to make proper movements requires more than just counting the number of times a predetermined angle is surpassed and warning the wearer of the incorrect movement. In order to prevent incorrect movement in hopes of reducing injuries, lost man hours, and workmen's compensation claims, a device must not only be able to record the frequency of improper movements, but also monitor the angular velocity and general tendencies of the wearer with regard to the unsafe movement habits. The angular velocity of any physical action affects the stretching and tautness of the muscle involved in the motion. Thus, information on angular velocity is important to monitoring and analyzing improper movement. Finally, the wearer must also be informed about the tendencies he has regarding his performance of a specific task. In particular, it is helpful to know whether improper movements occur more often in the morning or afternoon.

SUMMARY OF THE INVENTION

According to the present invention, the foregoing and other objects and advantages are attained by a system which may be used to monitor and train a wearer during physical movement. The system employs an electronic device which tracks and monitors an individual's motion through the use of a movement sensor capable of measuring data associated with the wearer's movement. The device also employs a user-programmable microprocessor which receives, interprets, stores and responds to the movement data based on customizable operation parameters, a clock connected to the microprocessor, memory for storing the movement and analysis data, a power source, a port for downloading the data from the device to other computation or storage devices contained within the system, and various input and output components. The downloadable, self-contained device can be worn at various positions along the torso or appendages being monitored depending on the specific physical task being performed. The device also monitors the speed of the movements made while the device is being worn. When a pre-programmed recordable event is recognized, the device records the time and date of the occurrence while providing feedback to the wearer via visual, audible and/or tactile warnings. Periodically, data from the device may be downloaded into an associated computer program which analyzes the data. The program can then format various reports to aid in recognizing and correcting trends in incorrect physical movement.

It is, therefore, an object of this invention to provide a user programmable training and safety device designed to observe and record the direction and frequency of physical movement of the wearer.

It is another object of this invention to provide a system which monitors, records and analyzes the time, date, angle of movement, and angular velocity of physical movement for subsequent interpretation.

It is still another object of this invention to monitor bi-directional movement of the torso about the spine during a lifting movement.

It is yet another object of this invention to detect and monitor a series of angles of movement and to visually and audibly warn the wearer as each angle limit is exceeded during physical movement.

It is yet another object of this invention to provide a device to assist in training an individual in proper posture while executing an identified physical activity.

To achieve these and other objects which will become readily apparent upon a reading of the attached disclosure and appended claims, an improved training and safety device is provided. Additional objects, advantages, and novel features of the invention will be set forth in part in the description which follows, and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF THE PREFERRED EMBODIMENT

Figure 1:
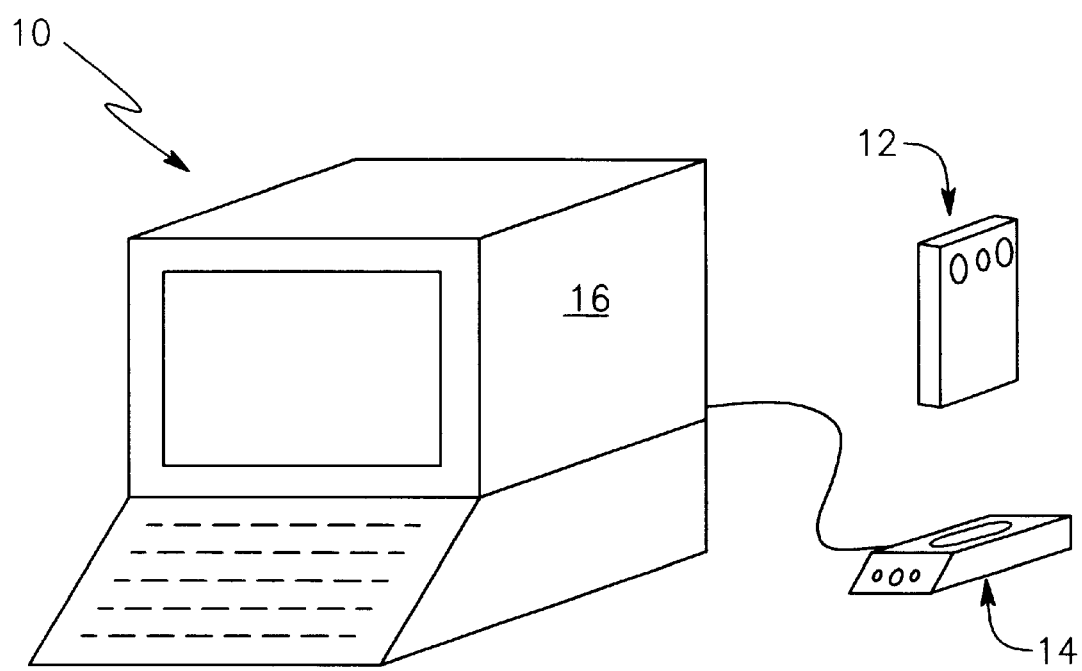
FIG. 1 is a plan view of the system of the present invention, including the movement measuring device, the download device, and the computer.

Reference is now made to FIG. 1 for a description of a preferred embodiment of the system 10 of the current invention. FIG. 1 shows the movement measuring device 12 positioned above a download device 14 connected to a computer 16. The movement measuring device 12 is designed to be physically attached to a user whose movements are to be monitored by the system 10. The self-contained movement measuring device 12 may be worn by the individual being monitored in a variety of positions based on the specific movement being observed, the particular application in which the device is used, and the convenience of the wearer.

Figure 2A:
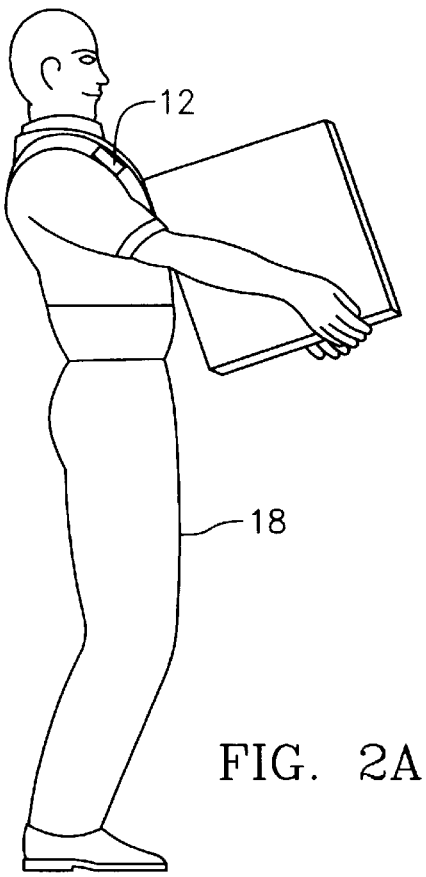
FIG. 2A is a plan view of a wearer showing a possible location for the movement measuring device in operation.
Figure 2B:
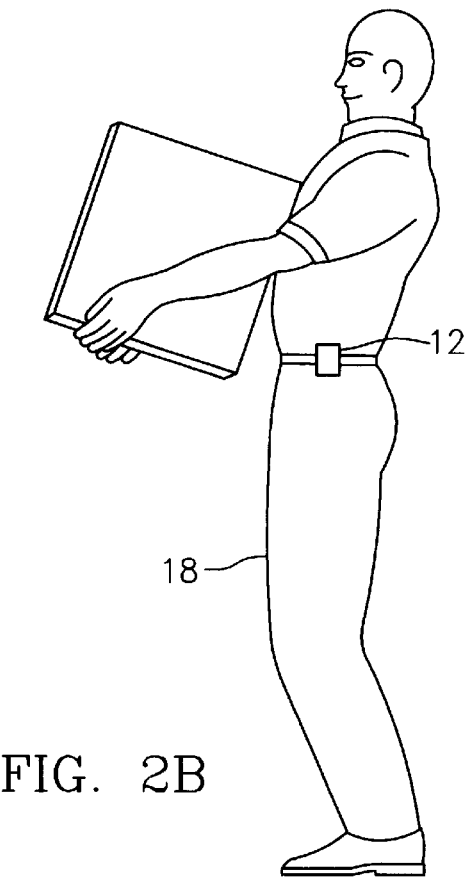
FIG. 2B is a plan view of a wearer showing another location for the device during operation.
Figure 2C:
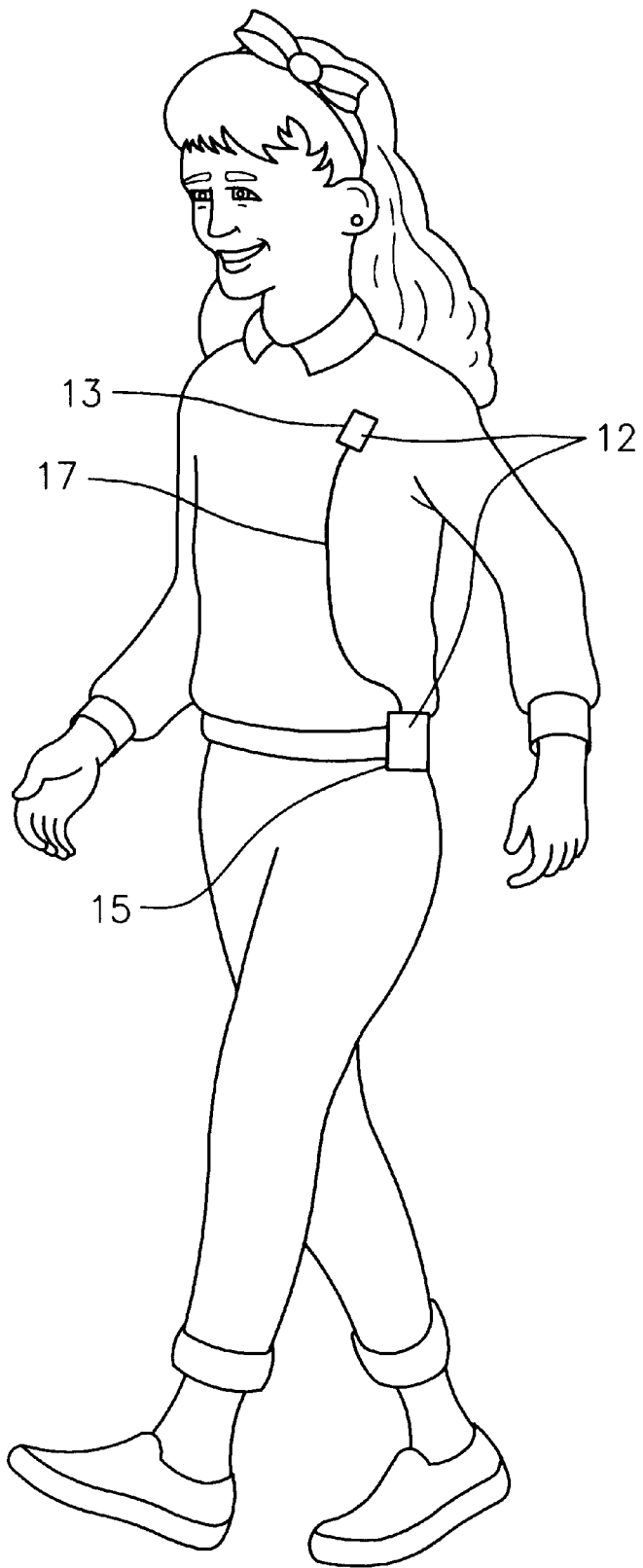
FIG. 2C is a plan view of a wearer showing the location of an alternative embodiment of the device of the present invention.

For example, FIG. 2A shows placement of the movement measuring device 12 on the upper torso of an individual 18. Placement of the device 12 at this location will allow monitoring of the flexion and extension of the spinal column during a lifting activity. Similarly, FIG. 2B shows placement of the movement measuring device 12 on the waist or hip of an individual 18. The movement measuring device 12 may be attached via a clip, Velcro, its own belt, or any other means known in the art. Placement of the device 12 on the belt as shown will also permit monitoring of the individual's movement during physical activity. In particular, the device 12 can monitor the forward and backward bending of the spine as well as lateral bending of the spine to aid in correct bending and lifting tasks. The device 12 is also capable of measuring the distance the wearer walks and how fast he walked. FIG. 2C shows another alternative embodiment of the movement measuring device 12. In this version, the movement sensor 13 is separate from the remaining components 15 of the device 12 and is electronically connected to the remaining components 15 via a cable 17 or other commonly used connector. Separating the measurement sensor 13 from the remaining components 15 in this way gives additional flexibility in the use of the device 12. The device 12 operates in the same manner as previously described; however, the movement sensor 13 can be placed anywhere on the individual's body. Again, the specific application will dictate where the movement sensor 13 should be placed. For example, if a monitored activity requires repeated arm movement, the sensor 13 may be placed anywhere along the individual's arm thereby monitoring and recording movement data for the arm.

Figure 3:
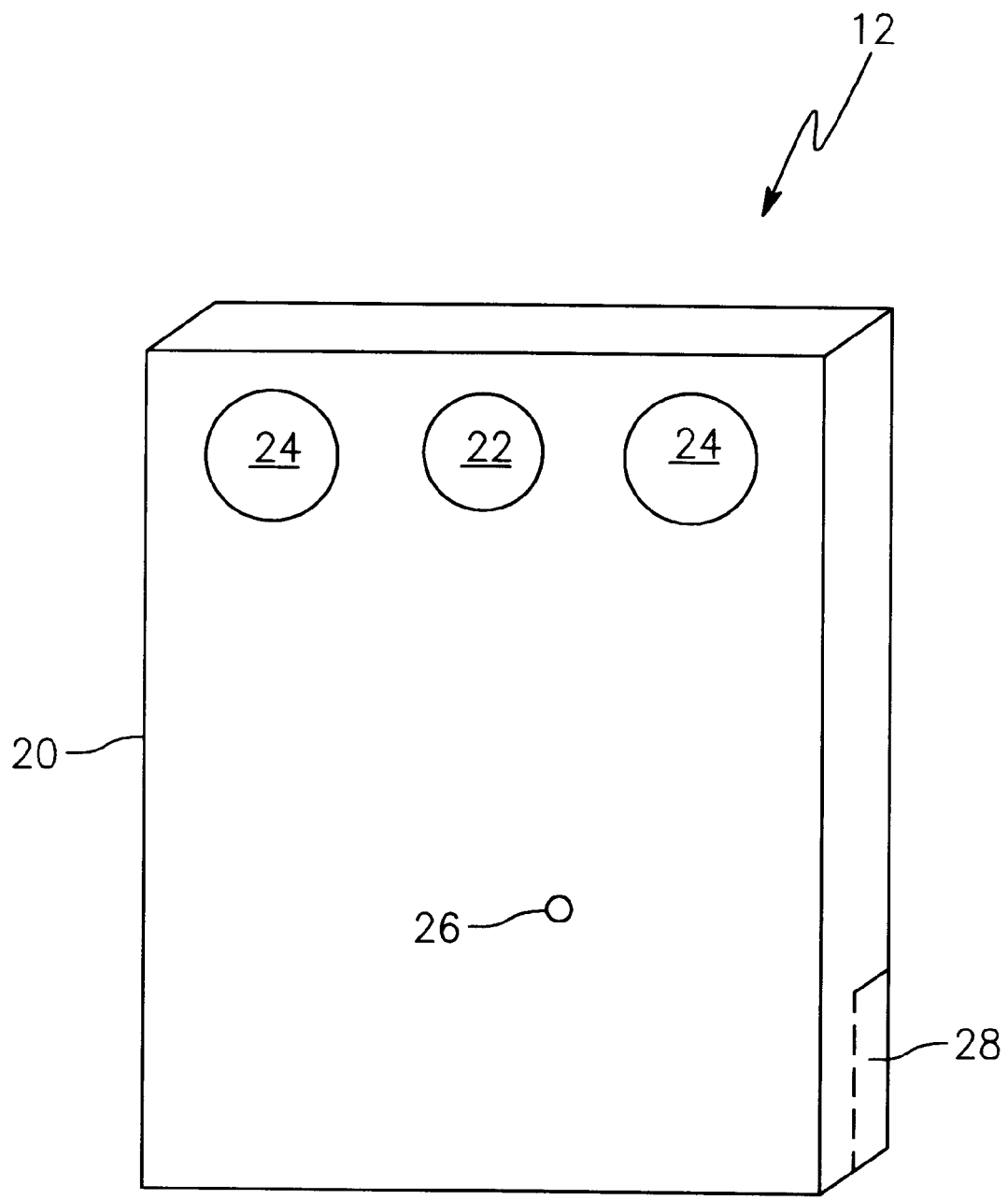
FIG. 3 is a perspective view of another alternative embodiment of the self-contained movement measuring device of the present invention.

FIG. 3 shows a more detailed view of the movement measurement device 12 which forms a crucial part of the previously described system along with its respective external components. The internal components of the movement measurement device 12 are housed in a casing 20. This casing 20 serves to protect the internal components and is most commonly made of hard molded plastic, although any suitable material may be substituted. Externally visible on the device 12 is at least one visual indicator 22 which is activated by the device 12 when appropriate. In one preferred embodiment, the visual indicator 22 is a bi-colored light emitting diode (LED) which is activated to notify the wearer when a predetermined angle of motion has been exceeded. Through different colors and blinking patterns, the visual indicator 22 signals many different conditions sensed by the device 12 including when the device 12 is turned on or off, when each of various angle limits is exceeded, and when downloading movement data recorded by the device 12. Alternatively, the visual indicator 22 may be a liquid crystal display or any other display device on which a variety of movement information may be shown. The movement measuring device 12 also contains user inputs 24. In the preferred embodiment, one user input 24 is an ON/OFF switch for controlling the operation of the device 12. Another user input 24 on the device 12 is a MUTE button which permits the wearer of the device to turn off any audible indicators. Typically, once an angle limit has been exceeded, the wearer will be notified through the illumination of a visual indicator, the sounding of an audible alarm, vibration of the device 12, or a combination thereof. In the case of an audible alarm, the MUTE button 24 may be used to turn off the alarm. Any sounds emitted by the device 12 are created by a speaker (not shown) behind the speaker cover 26 located in the external casing 20. Finally, the casing 20 contains a removable battery cover 28 over an externally accessible battery compartment (not shown) which allows the operator of the device 12 to replace the internal power source. In the preferred embodiment this power source is a 1.5 volt battery.

Figure 4:
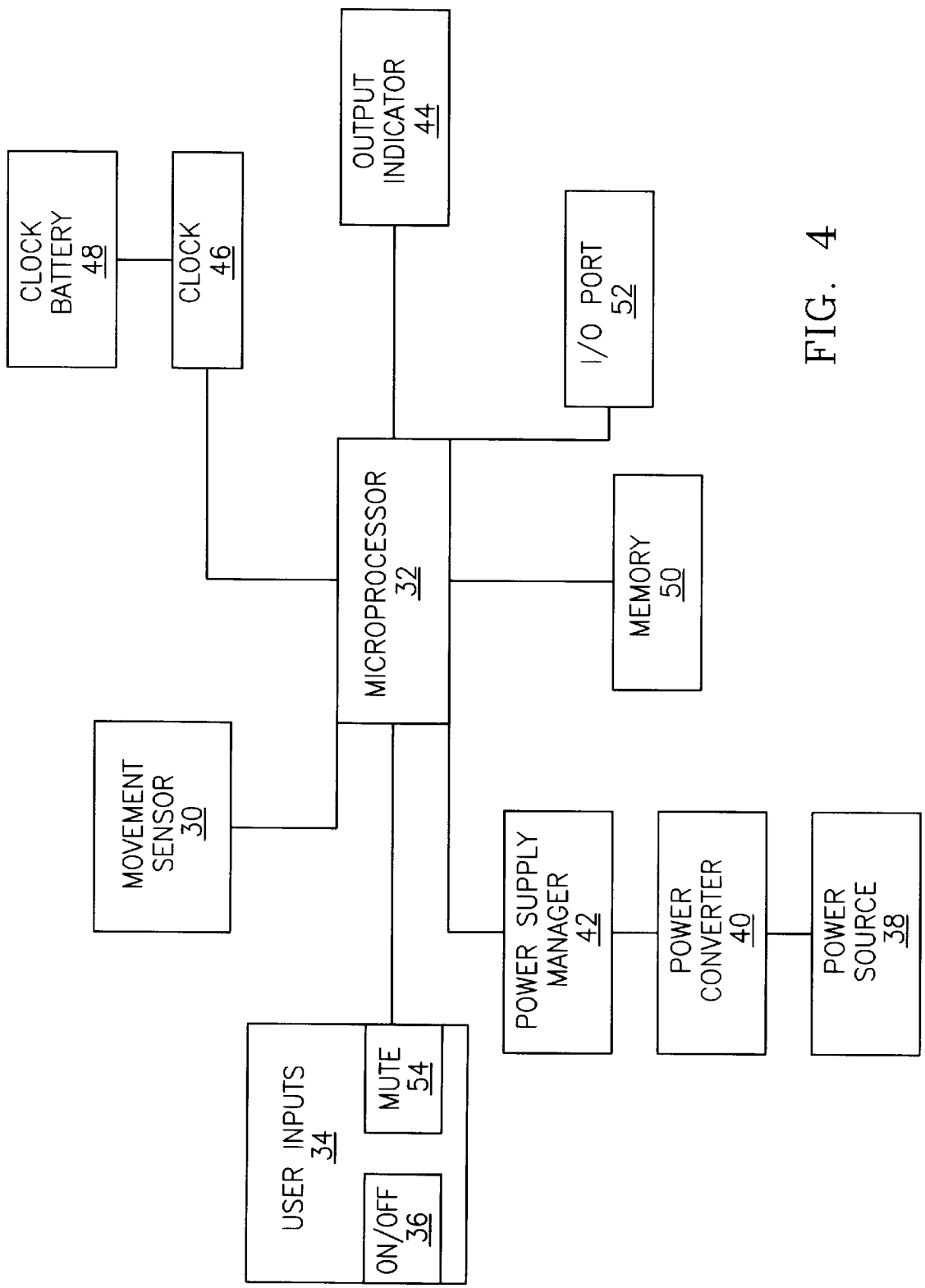
FIG. 4 is a block diagram of the movement measuring device of the present invention.

Reference is now made to a block diagram in FIG. 4 which shows the major internal components of the movement measuring device 12 and their interconnections. The device 12 includes a movement sensor 30 which detects movement and measures associated data such as angle, speed, and distance. The movement sensor 30 generates signals corresponding to the measurement data collected. In a preferred embodiment, the movement sensor 30 is an accelerometer which is capable of detecting angles of movement in multiple planes as well as the velocity at which the movement occurs. Alternatively, multiple accelerometers, each capable of measuring angles of movement in only one plane, may be oriented within the device 12 so that movement in multiple planes may be detected. Although many accelerometers are available on the market, the preferred embodiment uses Part No. AD22217 manufactured by Analog Devices of Norwood, Mass. This component is a low G, multi-axis accelerometer. The movement sensor 30 is electronically connected to a microprocessor 32 which receives the signals generated by the movement sensor 30 for analysis and subsequent processing. The microprocessor 32 not only analyzes and responds to the movement data signals from the sensor 30, but also controls the actions of all of the electronic components of the device 12. In a preferred embodiment, the microprocessor 32 is a Motorola MC68HC705C8AFN. It should be noted, however, that other low power, programmable microprocessors may be suitable. The microprocessor 32 constantly monitors the user inputs 34 and acts accordingly. For example, if the device is turned off, the microprocessor 32 monitors the ON/OFF user input 36 to detect when the device 12 is turned back on. Once an "ON" condition is detected, the microprocessor 32 powers up and runs its internal program. The internal program may be stored within read-only memory located in the microprocessor itself or in memory (not shown) located outside the microprocessor 32.

The components of the device 12 receive power from a power source 38. In a preferred embodiment the power source 38 is a 1.5 volt DC battery; however, other power sources, including alternating current, may be used. The power source 38 is connected to a power converter 40 if DC-DC or AC-DC conversion is required. In one embodiment the power converter 40 converts the 1.5 volt DC power supply from the battery to 3.3 volts DC for use with the other electronic components of the device 12.

Also connected between the power source 38 and the microprocessor 32 is a conventional power supply manager 42 such as part number ADM706TAR from Analog Devices. The power supply manager 42 performs several functions. If a low battery condition exists, the power supply manager 42 reports the problem to the microprocessor 32 so that the microprocessor 32 may indicate the condition to the user through one or more output indicators 44. The output indicators 44 consist of any combination of audible, visual, or tactile indicators for communicating with the wearer of the device. Audible indicators range from a single pitched tone to voice-synthesized messages in English or any foreign language. Visual indicators which could be used include single, monochromatic LEDs, multiple colored lights, and/or liquid crystal displays. The tactile indicator used in a preferred embodiment is a conventional vibrator mechanism which can be detected by the wearer. The power supply manager 42 also regulates the activity of the power converter 40 to insure that the proper voltage is constantly supplied to the device components.

The microprocessor 32 is connected to a clock 46 which is used as an internal clock for coordinating the functioning of the microprocessor 32. The clock 46 also serves as a real time clock to provide date and time information to the microprocessor 32. The clock 46 may have its own clock battery 48 or may receive power directly from power source 38.

The microprocessor 32 constantly monitors the movement data received from the movement sensor 30. The microprocessor 32 analyzes the movement data received from the sensor 30 and, based on its internal programming, responds to the data. If a recordable event occurs, the microprocessor 32 retrieves the date/time stamp from the clock 46 and records the event information along with the date/time stamp in memory 50. In a preferred embodiment, the memory is electrically erasable programmable read-only memory (EEPROM) so that, in the event the device should lose power, the information recorded in memory 50 will not be lost. The device also contains an input/output (I/O) port 52 which is connected to the microprocessor 32. The I/O port 52 is used to receive and transmit data collected by the device 12 between the microprocessor 32 and an external computer (not shown). In a preferred embodiment, the I/O port 52 is a serial port which includes an RS232 voltage level converter download board. Movement data stored in memory 50 can be sent through the I/O port 52 to a download device. In addition, user-programmable configuration information can be entered by a user via the external computer and uploaded through the I/O port 52 for use by microprocessor 32. The configuration information can encompass an array of information including, but not limited to, a series of notice levels corresponding to increasing angles of movement, an event threshold, a reset range for tilt determination, and a time period for entering idle mode. Once the device 12 is operating, the microprocessor 32 constantly checks to see if the angle movement information received from the movement sensor 30 indicates that the wearer has exceeded any of the pre-set notice levels. Depending on which notice level has been exceeded, the microprocessor 32 will cause the device 12 to react; i.e., by sounding an alarm. In addition, the microprocessor 32 will obtain the date/time stamp from the clock 46 and store that information along with the notice level that was exceeded into memory 50 for later analysis and reporting. Whenever an alarm is activated by the microprocessor 32, the MUTE control switch 54 may be used to deactivate the alarm; however, the corresponding movement data associated with the activation of the alarm is still recorded in memory 50. Furthermore, the date and time the MUTE control switch 54 was activated is also recorded by the device 12.

A significant feature of the device 12 of the present invention is that it gives instant information to the wearer at the moment of incorrect movement and also records the information for future reference and analysis. The device 12 monitors a wide variety of "events" and records each event with a date/time stamp. Many different types of "events" may be defined to be monitored by the device 12. As previously stated, any movement which surpasses any identified angle limit of movement (based on the specific physical task being accomplished and the range of motion needed to execute the task properly) is a standard recordable event. In addition, the device will record when no discernable movement has occurred for a predetermined amount of time (idle function), when the wearer has pressed the MUTE switch in response to an alarm (MUTE function), when the wearer's speed of movement exceeds a predefined speed (quickness function), when the device is turned on or off, when a low battery warning has been issued, when the battery is changed, when the device has been tampered with (such as removing the battery before a low battery condition has been detected), when the device is tilted outside of a specified range for a designated period of time, and when the device has measured a predetermined maximum number of particular angle limits reached. These functions are further described hereinbelow.

Whenever an incorrect user movement is sensed by the device 12, the angular limit notice as programmed by the user is given only once. Before the device 12 can reset itself to be able to give that same angle notice on the next incorrect movement, the device 12 must return to a predetermined position (usually the upright position). If the device 12 is maintained outside of its predefined reset range for a designated period of time after an angle limit has been exceeded, a "tilt" event will be recorded and an alarm may be activated. When this situation occurs, the device 12 must be returned to its defined reset position, or the MUTE button must be pressed. The device 12 is also programmed to automatically enter a power saving mode when no motion has been detected for a given amount of time. This "idle" function event is recorded by the microprocessor 32 to indicate that the device is either not being worn or is not being used properly. The device 12 maintains the minimum amount of operating power required to detect the next movement so that, once movement is detected, the device 12 exits the idle mode and records the date and time when the exit occurred.

The device 12 will record any attempted tampering. In a preferred embodiment, this event occurs when the battery is removed before a low battery condition is detected by the device. The device 12 will also inform the wearer when the battery is low. In the preferred embodiment, the device 12 has two batteries, a battery which operates the device 12 and an internal time clock battery. The internal clock battery powers the time clock 46 and aids in other operations of the device 12 when the voltage drops on the device battery. The microprocessor 32 and memory 50 do not lose information when battery power is lost from either battery.

As previously mentioned, the device 12 is completely user programmable via an external computer. These user programmed operation parameters are uploaded to the microprocessor 32 through the download device (not shown). The user may program the microprocessor 32 with an array of functions for the device 12 to perform. Primary among these is the ability to change the angular levels at which notices will be generated in order to fulfill particular application needs. In this way, the user may choose the angular positions at which he wants to be warned when they are exceeded. In the preferred device, up to three angle limits may be monitored by the device; however, any number of angles may be tracked depending upon the application. Each angle limit can be degree specific or extend over a range of degrees. When a range is used, the user specifies the starting and incremental values in degrees. Thus, an angle limit may be set to occur every five degrees beginning with an initial angle limit value. The movement sensor 30 used in the preferred embodiment can measure angles to within plus or minus 0.5° and as often as 1000 times a second. The most common use for the angle range limits is when the device 12 is worn on the hip since angle measurements cannot be made as accurately there. In contrast, when the device 12 is worn on the upper torso, results can be measured more accurately and the device 12 can be set to measure each degree of movement.

As mentioned above, once a wearer of the device 12 exceeds the first defined angle limit, a notice for that limit is given to the wearer. The notice may be a combination of a visual warning, a tactile warning, and/or an audible warning. The microprocessor 32 also stores the specific angle limit which was exceeded along with the date/time stamp. Upon exceeding the second defined angle, the wearer is issued a second notice which may be the same as or different from the first notice. These different notice characteristics may include a change in pitch for audible alarms, a difference in duration for tactile alarms, and/or a blinking, different colored, or other visual warning.

The "quickness" function of the device 12 measures the speed of an associated physical movement made by the wearer and was developed to address the following problem. In essence, the warning notice due to exceeding a first angle may be overridden by the warning notice for a second angle, thus appearing to give only the second notice. The device 12 may be programmed to recognize when this occurs and to indicate that the associated physical activity was performed by the wearer with excessive speed. If so programmed, the device 12 will record both notices, and the microprocessor 32 will record a quickness violation for further analysis and reporting by the computer. The device 12 may also include an event threshold function in its programming. This feature allows the user of the device 12 who has access to the download capabilities and the analysis software hereinafter described to determine a maximum number of incorrect movements ("events") allowed in a predetermined time period by event type. In addition, the user may program a certain response, such as shutting down the device 12 entirely, emitting a special alarm, and/or recording the date and time each event threshold was met. In a preferred embodiment, if the device 12 is programmed for shut down upon reaching the event threshold, the device 12 will require downloading to the computer 16 and being reset before it can be operated again. This feature serves to alert the responsible party of a potential problem that must be dealt with immediately via retraining or any other means the responsible party deems necessary.

The device 12 also has additional functions and capabilities. Each unit can be assigned to a specific individual, patient or employee and later reassigned to a different person through the use of specific identification numbers. In a preferred embodiment, the device 12 requires a download of all movement data stored in memory under a previous identification number before it can be reassigned. Further, the download information along with the specific user identification number can be downloaded to the computer 16 only once in order to avoid duplicate records.

As generally described above, the system and device 12 of the present invention have practical application in a number of situations. They may be used in medical applications requiring the monitoring of physical movement. Among such applications is physical therapy which may be conducted either by the patient in the patient's home or by medical professionals in a medical environment. More significantly, the device and system have application in an industrial setting, particularly manufacturing, where workers are required to perform repetitive manual tasks. Supervising employers can use the device and system to insure that employees are performing their tasks properly while minimizing the risk of employee injury.

By virtue of the sophisticated nature of the microprocessor 32, the device 12 can fulfill these additional business, industry and medical needs. Furthermore, wireless capabilities may be added to the device 12 to allow downloading of information from the device 12 to a computer 16 without the need for cables or docking stations. In yet another embodiment, the radio frequency capability may allow the user to wear minimal hardware (consisting primarily of the movement sensor) on the body while transmitting the details of each physical movement to a remote microprocessor 32 for analysis and storage.

Once the data from the device 12 has been downloaded to the computer 16, software running on the computer 16 is used to interpret the data and produce a number of reports and histories. This history information may include, but is not limited to, the dates and times when the device 12 was turned on and off; the number, with dates and times, of each notice given along with the type of notice; the number, date and time the device 12 reached an event threshold; when, how long, and how many times the device 12 powered down; the date and time the device 12 was muted; the date and time when the battery was changed; the date and time when the battery was tampered with; and the last time the device 12 was downloaded. Any of the above-mentioned predefined reports may be generated; in addition, the user may program additional reports and histories specific to the application to be monitored.

Figure 5B:
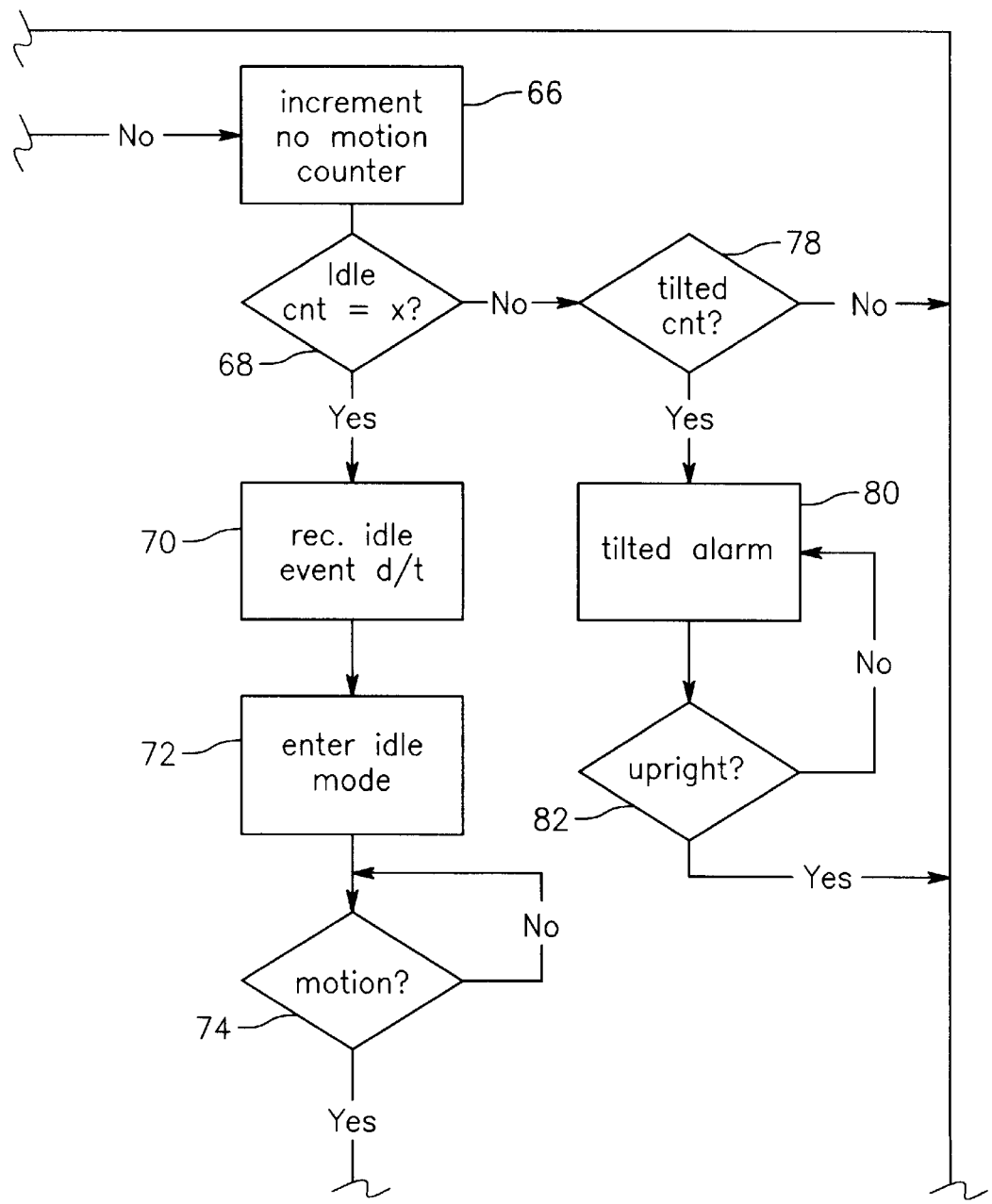
FIG. 5 is a flowchart of the steps performed by the microprocessor in operating the movement measuring device.
Figure 5C:
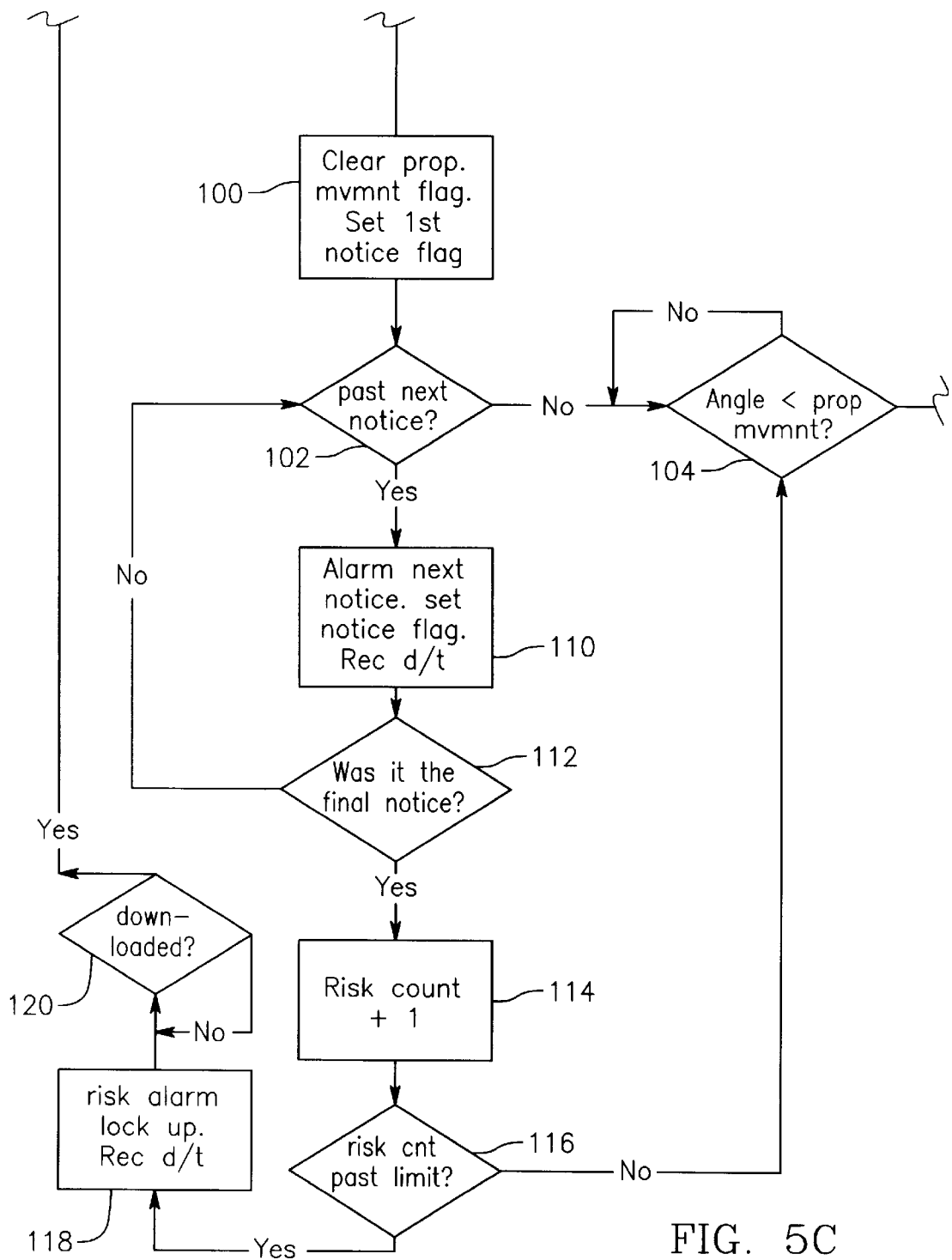
Figure 5D:
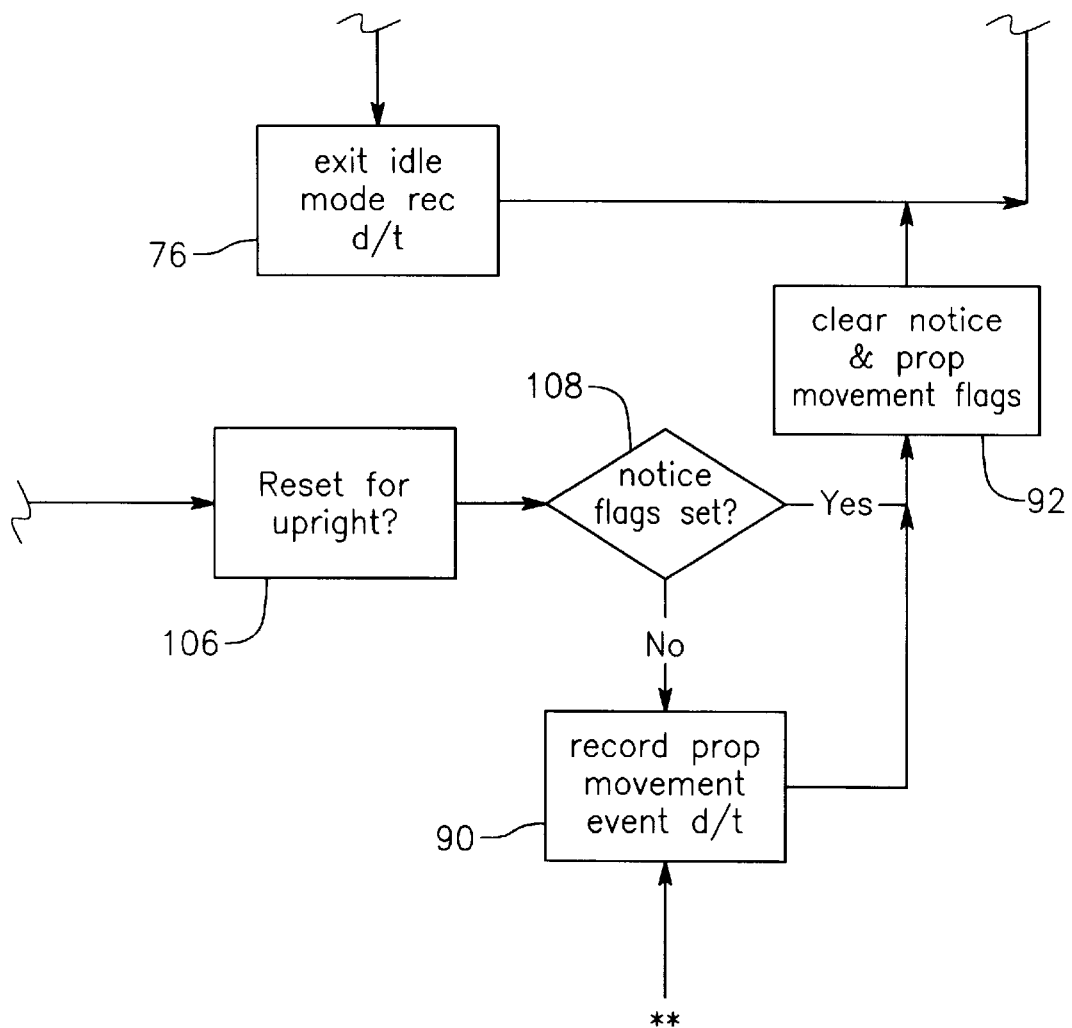

FIG. 5 is a flowchart of the steps executed by the microprocessor 32 in the movement measurement device 12 to recognize and record movement data. Referring to FIG. 5, when the device 12 is off, the microprocessor 32 constantly checks for a change in the ON/OFF state 60 by polling the ON/OFF switch to see if it has been switched to the ON position. Once the microprocessor 32 detects that the device 12 has been turned on, the microprocessor 32 conducts some basic initialization and housekeeping functions 62. This may include checking memory to ensure angle limits have been entered, verifying that angle limits are increasing in value (i.e., the second angle limit is not smaller than the first), and initializing internal program parameters. Then the microprocessor 32 checks to see whether any motion has been detected 64 by the movement sensor 30. If no motion has been detected, the microprocessor 32 will increment a "no-motion" counter 66. The microprocessor 32 then checks whether the no-motion counter has reached a predefined number of cycles indicating that the device should power down. If the requisite number of cycles indicating idle mode have elapsed, the microprocessor records the idle event (along with the date and time stamp) in memory, and the device enters the idle mode 72. Once in idle mode, the microprocessor repeatedly checks for motion 72. As long as no motion occurs, the device remains in idle mode. Once motion is detected, the microprocessor records an event that the device has exited idle mode (with the corresponding date and time) 76. The microprocessor then returns to step 64 where it again attempts to detect motion. If the no-motion counter has not reached the preset limit corresponding to idle mode, the microprocessor will check to see whether the device has remained outside of its predefined reset range for a designated amount of time 78. If not, the microprocessor reexecutes the cycle for detecting motion 64. If, however, the microprocessor recognizes a tilt event, an alarm corresponding to a tilt event is activated 80. Once the microprocessor has recognized a tilt event, it repeatedly checks whether the device has been moved back within its reset range 82. If it has not, the microprocessor continues to activate the tilt alarm. Once the device has been returned to within its reset range, the microprocessor checks again for motion 64.

Once the microprocessor detects motion in step 64, the first thing it does is clear the no-motion counter 84. The microprocessor then checks to see whether it has recorded a "proper movement" in the past 86. If no proper movement has occurred, the microprocessor checks whether the proper movement flag has been set 88. If the proper movement flag has not been set, the microprocessor returns to its initial motion checking step 64. If, however, the proper movement flag has been set, the microprocessor will record the occurrence of a proper movement event along with the date/time stamp 90. The microprocessor then clears all notice and the proper movement flags in step 92 and returns to the motion detection step 64. If, on the other hand, the microprocessor has detected a prior proper movement 86, it so indicates by setting the proper movement 94. The microprocessor then checks whether the first angle limit has been exceeded 96. If this first limit has not yet been exceeded, the microprocessor returns to the motion detection step 64. If the first angle limit has been exceeded, the microprocessor activates the appropriate alarm and records the event along with the date and time 98. The microprocessor then clears the proper movement flag and sets the first angle notice flag 100. The microprocessor then checks whether the device has moved beyond the next angle limit 102. If not, the microprocessor checks whether the angle is less than that required to constitute a proper movement 104. If not, then the microprocessor continues to check whether the angle of movement is less than a proper movement angle. If the angle is less than that constituting a proper movement, the microprocessor triggers a reset flag indicating that the device has been reset 106. After reset, the microprocessor checks whether any of the angle limits have been exceeded thereby setting any of the notice flags 108. If any notice flags have been set, the microprocessor will perform step 92 to clear all of the notice flags and reset the proper movement flag. If none of the notice flags have been set before the device was reset, the microprocessor will perform step 90 to record a proper movement event along with the date and time. It then continues processing at step 92.

Once the angle of movement detected exceeds the next angle limit, the microprocessor will record the corresponding notice event along with the date and time and activate the appropriate notice alarm in step 110. The microprocessor then checks if the last movement exceeded the final angle limit at step 112. If not, then the process returns to step 102 to check for movement beyond the next angle limit. If the final notice event was detected, then the microprocessor will increment the event threshold counter by one at step 114 if this option has been selected by the user. Next, the microprocessor will check to see whether the event threshold limit has been reached 116. If not, the microprocessor will perform step 104 until the device is reset due to the movement angle being less than that required for a proper movement. If the event threshold has been reached, then the microprocessor will record the event threshold, activate the associated alarm, and shut down the device 118. The microprocessor will prevent the device from operating any further until its information has been downloaded 120. Once the stored data has been downloaded, the microprocessor returns to its initial motion detection step 64 for further operation.

As previously alluded to herein, the device and system of the present invention can be used in a wide number of different applications requiring monitoring and feedback of physical movement. In particular, the device and system have various medical applications including rehabilitation and physical therapy associated with an injured patient. The movement sensor is simply attached to the appropriate body part requiring monitoring, and data collection is then commenced. Besides providing the operator with instant feedback regarding the physical movement being monitored, a variety of data may be collected from the number of movement repetitions meeting or exceeding a required range to the determination and tracking of maximum range-of-motion mobility of an injured patient for later analysis. While the device and system may be operated by a medical professional in a supervisory capacity, both are simple enough to be used by an individual patient alone with download and analysis by the medical professional at a later time.

The device also has excellent application to the monitoring and analysis of physical labor performed by employees. The devices may be passed out to employees having repetitive physical tasks so that proper safety in performing the tasks, such as lifting, may be practiced. Each device can be assigned to a particular individual for a specified amount of time and programmed to monitor that individual's physical tasks. After the device is turned in, its collected information can be downloaded to the system for reporting and analysis purposes based on specific movement limits and other operational parameters programmed into the device for the particular movement being monitored. Improper movements made by the individual during the time period in question are identified, and the employee can be notified in order to make necessary corrections to the way the task is performed in order to avoid injury resulting from improper movement. The device can be used again later to ensure that the employee continues to exercise the movement guidelines as previously instructed.

The device also has application in the area of sports. For example, it may be worn by a golfer in order to monitor torso, waist, shoulder and arm movement during various drives and putts. The data collected by the device may then be used as a tool to aid in the analysis and improvement of the individual's stroke technique. Use of the device is not limited to golf but may be used for any number of sports, including football, baseball, basketball, or tennis. And, due to the unique programmability of the device, it has more than one application within any single sport. For example, in baseball, the device and system may be used to improve technique associated with hitting or with throwing.

Still other objects and advantages of the present invention will become readily apparent to those skilled in this art from the detailed description, wherein multiple preferred embodiments of the invention are shown and described, simply by way of illustration of the best mode contemplated by the inventor for carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive. Variations in the description likely to be conceived of by those skilled in the art still fall within the breadth and scope of the disclosure of the present invention. The primary import of the present invention lies in its compact size, ease of use, and detailed information gathering and reporting features. Its benefits derive from the versatility of its monitoring capabilities as well as the specific applications for which it may be used. Again, it is understood that other applications of the present invention will be apparent to those skilled in the art upon reading the preferred embodiments and consideration of the appended claims.

We claim:

1. A portable, self-contained device for monitoring movement of body parts during physical activity, said device comprising:
   a movement sensor capable of measuring data associated with unrestrained movement in any direction and generating signals indicative of said movement;
   a power source;
   a microprocessor connected to said movement sensor and to said power source, said microprocessor capable of receiving, interpreting, storing and responding to said movement data based on user-defined operational parameters;
   at least one user input connected to said microprocessor for controlling the operation of said device;
   a real-time clock connected to said microprocessor;
   memory for storing said movement data; and
   an output indicator connected to said microprocessor for signaling the occurrence of user-defined events;
   wherein said movement sensor measures the angle and velocity of said movement.

2. The device of claim 1 further comprising at least one input/output port connected to said microprocessor for downloading said data and uploading said operational parameters to and from a computer.

3. The device of claim 1 wherein said device is compact and weighs less than one pound.

4. The device of claim 1 wherein said movement sensor comprises at least one accelerometer.

5. The device of claim 1 wherein said movement sensor can simultaneously detect real time movement along at least two orthogonal axes.

6. The device of claim 1 wherein said movement sensor is housed separately from said microprocessor.

7. The device of claim 1 wherein said monitored body part movement is torso or limb movement.

8. The device of claim 1 wherein said data measured by said movement sensor includes the distance of said movement.

9. The device of claim 1 wherein said output indicator is visual.

10. The device of claim 1 wherein said output indicator is audible.

11. The device of claim 1 wherein said output indicator is tactile.

12. The device of claim 1 wherein said user input is a switch.

13. A system to aid in training and safety during physical activity, said system comprising
   a portable, self-contained movement measuring device, said movement measuring device further comprising
      a movement sensor capable of measuring data associated with unrestrained movement in any direction and generating signals indicative of said movement;
      a power source;
      a microprocessor connected to said power source, said microprocessor capable of receiving, interpreting, storing and responding to said movement data based on user-defined operational parameters;
      at least one user input connected to said microprocessor for controlling the operation of said device;
      a real-time clock connected to said microprocessor;
      memory for storing said movement data;
      at least one input/output port connected to said microprocessor for downloading said data and uploading said operational parameters; and
      an output indicator connected to said microprocessor;
      a computer running a program capable of interpreting and reporting said movement data based on said operational parameters; and
      a download device electronically connected to said movement measuring device and said computer for transmitting said movement data and operational parameters between said movement measuring device and said computer for analysis, reporting and operation purposes;
   wherein said movement sensor measures the angle and velocity of said movement.

14. The system of claim 13 wherein said computer is a personal computer.

15. The system of claim 13 wherein said computer is connected to a network of other computers.

16. The system of claim 13 wherein said download device is a physical docking station.

17. The system of claim 13 wherein said download device is a wireless device.

18. The system of claim 17 wherein said wireless device uses radio frequency.

19. The system of claim 17 wherein said wireless device uses infrared light.

20. A method to monitor physical movement of a body part comprising the steps of:
   attaching a portable, self-contained movement measuring device to said body part for measuring unrestrained movement in any direction;
   measuring data associated with said physical movement;
   interpreting said physical movement data based on user-defined operational parameters and a real-time clock; and
   storing said data in memory.

21. The method of claim 20 wherein said physical movement data includes velocity data of said movement, angle measurement data taken along at least two orthogonal axes, and related date and time data.

22. The method of claim 21 further comprising the step of defining said parameters for a specific physical movement prior to said interpreting step.

23. The method of claim 21 further comprising the step of downloading said data from said movement measuring device to a computer for reporting and analysis purposes.

24. The method of claim 21 wherein said interpreting step comprises teaching an individual how to properly perform said physical movement.

25. The method of claim 20 wherein said movement measuring device is an accelerometer.

26. The method of claim 20 further comprising the step of providing real time feedback regarding said movement.

27. The method of claim 26 wherein said physical movement is physical labor.

28. The method of claim 26 wherein said physical movement is an exercise related to medical treatment.

29. The method of claim 26 wherein said physical movement is an exercise to improve technique related to an athletic skill.

* * * * *

(12) EX PARTE REEXAMINATION CERTIFICATE (10541st)
United States Patent
Brann

(10) Number: US 6,059,576 C1
(45) Certificate Issued: Mar. 17, 2015

(54) TRAINING AND SAFETY DEVICE, SYSTEM AND METHOD TO AID IN PROPER MOVEMENT DURING PHYSICAL ACTIVITY

(75) Inventor: Theodore L. Brann, Mission, TX (US)

(73) Assignee: Logantree L P, Boerne, TX (US)

Reexamination Request:
No. 90/013,201, Apr. 4, 2014

Reexamination Certificate for:
Patent No.: 6,059,576
Issued: May 9, 2000
Appl. No.: 08/976,228
Filed: Nov. 21, 1997

(51) Int. Cl.
*A61B 5/11* (2006.01)
*A63B 24/00* (2006.01)

(52) U.S. Cl.
CPC .......... *A61B 5/1116* (2013.01); *A63B 2220/40* (2013.01); *Y10S 482/901* (2013.01)
USPC ............... 434/247; 600/595; 482/8; 482/901; 702/101; 601/34

(58) Field of Classification Search
None
See application file for complete search history.

(56) References Cited

To view the complete listing of prior art documents cited during the proceeding for Reexamination Control Number 90/013,201, please refer to the USPTO's public Patent Application Information Retrieval (PAIR) system under the Display References tab.

*Primary Examiner* — Danton DeMille

(57) ABSTRACT

An electronic device, system and method to monitor and train an individual on proper motion during physical movement. The system employs an electronic device which tracks and monitors an individual's motion through the use of an accelerometer capable of measuring parameters associated with the individual's movement. The device also employs a user-programmable microprocessor which receives, interprets, stores and responds to data relating to the movement parameters based on customizable operation parameters, a real-time clock connected to the microprocessor, memory for storing the movement data, a power source, a port for downloading the data from the device to other computation or storage devices contained within the system, and various input and output components. The downloadable, self-contained device can be worn at various positions along the torso or appendages being monitored depending on the specific physical task being performed. The device also detects the speed of movements made while the device is being worn. When a preprogrammed recordable event is recognized, the device records the time and date of the occurrence while providing feedback to the wearer via visual, audible and/or tactile warnings.

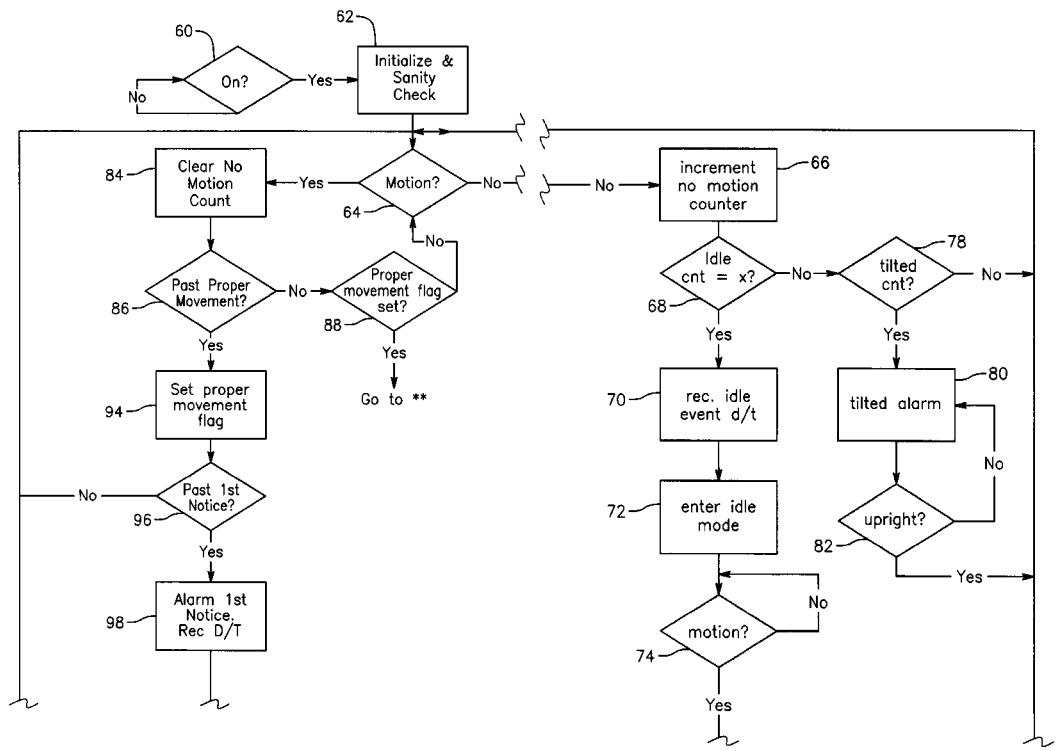

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 13 and 20 are determined to be patentable as amended.

Claims 2-12, 14-19 and 21-29, dependent on an amended claim, are determined to be patentable.

New claims 30-185 are added and determined to be patentable.

1. A portable, self-contained device for monitoring movement of body parts during physical activity, said device comprising:
   a movement sensor capable of measuring data associated with unrestrained movement in any direction and generating signals indicative of said movement;
   a power source;
   a microprocessor connected to said movement sensor and to said power source, said microprocessor capable of receiving, interpreting, storing and responding to said movement data based on user-defined operational parameters, *detecting a first user-defined event based on the movement data and at least one of the user-defined operational parameters regarding the movement data, and storing first event information related to the detected first user-defined event along with first time stamp information reflecting a time at which the movement data causing the first user-defined event occurred*:
   at least one user input connected to said microprocessor for controlling the operation of said device;
   a real-time clock connected to said microprocessor; memory for storing said movement data; and
   an output indicator connected to said microprocessor for signaling the occurrence of user-defined events;
   wherein said movement sensor measures the angle and velocity of said movement.

13. A system to aid in training and safety during physical activity, said system comprising
    a portable, self-contained movement measuring device, said movement measuring device further comprising
       a movement sensor capable of measuring data associated with unrestrained movement in any direction and generating signals indicative of said movement;
       a power source;
       a microprocessor connected to said power source, said microprocessor capable of receiving, interpreting, storing and responding to said movement data based on user-defined operational parameters, *detecting a first user-defined event based on the movement data and at least one of the user-defined operational parameters regarding the movement data, and storing first event information related to the detected first user-defined event along with first time stamp information reflecting a time at which the movement data causing the first user-defined event occurred;*
       at least one user input connected to said microprocessor for controlling the operation of said device;
       a real-time clock connected to said microprocessor; memory for storing said movement data;
       at least one input/output port connected to said microprocessor for downloading said data and uploading said operational parameters; and
       an output indicator connected to said microprocessor;
    a computer running a program capable of interpreting and reporting said movement data based on said operational parameters; and
    a download device electronically connected to said movement measuring device and said computer for transmitting said movement data and operational parameters between said movement measuring device and said computer for analysis, reporting and operation purposes;
    wherein said movement sensor measures the angle and velocity of said movement.

20. A method to monitor physical movement of a body part comprising the steps of:
    attaching a portable, self-contained movement measuring device to said body part for measuring unrestrained movement in any direction;
    measuring data associated with said physical movement;
    interpreting, *using a microprocessor included in the portable, self-contained movement measuring device,* said physical movement data based on user-defined operational parameters and a real-time clock; [and]
    storing said data in memory;
    *detecting, using the microprocessor, a first user-defined event based on the movement data and at least one of the user-defined operational parameters regarding the movement data; and*
    *storing, in said memory, first event information related to the detected first user-defined event along with first time stamp information reflecting a time at which the movement data causing the first user-defined event occurred.*

30. *The device of claim 1, wherein said microprocessor is configured to store, in said memory, date information associated with the first time stamp information.*

31. *The device of claim 1, wherein said microprocessor is configured to retrieve said first time stamp information from said real-time clock and associate the retrieved first time stamp information with said first user-defined event.*

32. *The device of claim 31, wherein said microprocessor is configured to retrieve said first time stamp information from said real-time clock based on the detection of the user-defined event.*

33. *The device of claim 1, wherein said memory is configured to continue to store said movement data in response to battery power being lost from said power source.*

34. *The device of claim 1, wherein said movement sensor is configured to continuously check for said movement.*

35. *The device of claim 34, wherein said microprocessor is configured to continuously interpret, based on the user-defined operational parameters, said movement data received from said movement sensor.*

36. *The device of claim 1, wherein said output indicator is configured to display information signaling the occurrence of the first user-defined event based on the detection of the first user-defined event.*

37. The device of claim 36, wherein said output indicator is configured to display said information signaling the occurrence of the first user-defined event based on said first time stamp information.

38. The device of claim 1, wherein said output indicator is configured to display information signaling the occurrence of the first user-defined event based on the detection of the first user-defined event and the first time stamp information.

39. The device of claim 1, wherein said at least one of the user-defined operational parameters is a predetermined threshold, and said first user-defined event occurs when the movement data reaches the predetermined threshold.

40. The device of claim 39, wherein said output indicator is configured to display information signaling the occurrence of the first user-defined event when the movement data reaches the predetermined threshold.

41. The device of claim 39, wherein said memory is configured to store said first event information indicating that the predetermined threshold is met.

42. The device of claim 41, wherein said memory is configured to store the first time stamp information in association with said first event information.

43. The device of claim 1, wherein said output indicator is configured to indicate a low battery condition of the device.

44. The device of claim 9, wherein said output indicator is selected from the group consisting of single monochromatic LEDs, multiple colored lights, and liquid crystal displays.

45. The device of claim 1, wherein said movement data stored in the memory is configured to be downloaded to a computer.

46. The device of claim 45, further comprising:
software configured to communicate with external software, wherein the external software is configured to present the downloaded movement data to the user.

47. The device of claim 46, wherein said external software is configured to run on the computer.

48. The device of claim 47, wherein said downloaded movement data is configured to be analyzed by said user via said external software.

49. The device of claim 46, wherein said external software is configured to interpret said movement data and produce at least one report.

50. The device of claim 46, wherein said external software is configured to interpret said movement data and produce at least one history report.

51. The device of claim 50, wherein said at least one history report includes dates and times of said movement data.

52. The device of claim 46, wherein said external software is configured to allow the user to program additional reports and histories with respect to said movement data of said user.

53. The device of claim 45, wherein said movement data is configured to be downloaded to said computer via a wired connection.

54. The device of claim 45, wherein said movement data is configured to be downloaded to said computer via a wireless connection.

55. The device of claim 39, wherein the output indicator is configured to provide a visual indicator to the user regarding the predetermined threshold being reached.

56. The device of claim 1, wherein the memory is configured to store the user-defined operational parameters, the user-defined operational parameters comprising a plurality of thresholds respectively corresponding to a plurality of notifications, wherein each time the movement data reaches one of the plurality of the thresholds, the microprocessor is configured to detect that one of the user-defined events occurred.

57. The device of claim 56, wherein when the microprocessor detects that one of the user-defined events occurred based on the movement data reaching one of the plurality of the thresholds, the output indicator displays a corresponding one of the notifications indicating that one of the user-defined events has occurred.

58. The device of claim 56, wherein the plurality of thresholds are different from each other.

59. The device of claim 56, wherein the plurality of notifications are different visual indicators.

60. The device of claim 59, wherein at least one of the visual indicators includes a blinking indicator.

61. The device of claim 39, wherein said microprocessor is configured to detect occurrence of the first user-defined event by comparing said movement data to said predetermined threshold.

62. The device of claim 1, wherein said device is configured to be placed on said user's arm to monitor and record said movement data.

63. The device of claim 62, wherein said movement sensor is configured to measure movement of said user's arm.

64. The device of claim 1, wherein said movement sensor is configured to measure a walking distance.

65. The device of claim 64, wherein said device is configured to be wearable by the user, and said movement sensor is configured to measure said walking distance of said user.

66. The device of claim 1, wherein said microprocessor is configured to store, in said memory, date information associated with the first time stamp information,
wherein said movement sensor is configured to continuously check for said movement,
wherein said output indicator is configured to display information signaling the occurrence of the first user-defined event based on the detection of the first user-defined event and the first time stamp information,
wherein the device further comprises software configured to communicate with external software configured to run on a computer and present the downloaded movement data,
wherein said external software is configured to produce at least one report based on said movement data,
wherein the memory is configured to store the user-defined operational parameters, the user-defined operational parameters comprising a plurality of thresholds respectively corresponding to a plurality of notifications, wherein each time the movement data reaches one of the plurality of the thresholds, the microprocessor is configured to detect that one of the user-defined events occurred,
wherein said device is configured to be placed on said user's arm to monitor and record said movement data,
wherein said movement sensor is configured to measure movement of said user's arm.

67. The system of claim 13, wherein said microprocessor is configured to store, in said memory, date information associated with the first time stamp information.

68. The system of claim 13, wherein said microprocessor is configured to retrieve said first time stamp information from said real-time clock and associate the retrieved first time stamp information with said first user-defined event.

69. The system of claim 68, wherein said microprocessor is configured to retrieve said first time stamp information from said real-time clock based on the detection of the first user-defined event.

70. The system of claim 13, wherein said memory is configured to continue to store said movement data in response to battery power being lost from said power source.

71. The system of claim 13, wherein said movement sensor is configured to constantly checks for said movement.

72. The system of claim 71, wherein said microprocessor is configured to continuously interpret, based on the user-defined operational parameters, said movement data received from said movement sensor.

73. The system of claim 13, wherein said output indicator is configured to display information signaling the occurrence of the first user-defined event based on the detection of the first user-defined event.

74. The system of claim 73, wherein said output indicator is configured to display said information signaling the occurrence of the first user-defined event based on said first time stamp information.

75. The system of claim 13, wherein said output indicator is configured to display information signaling the occurrence of the first user-defined event based on the detection of the first user-defined event and the first time stamp information.

76. The system of claim 13, wherein said at least one of the user-defined operational parameters is a predetermined threshold, and said first user-defined event occurs when the movement data reaches the predetermined threshold.

77. The system of claim 76, wherein said output indicator is configured to display information signaling the occurrence of the first user-defined event when the movement data reaches the predetermined threshold.

78. The system of claim 78, wherein said memory is configured to store said first event information indicating that the predetermined threshold is met.

79. The system of claim 78, wherein said memory is configured to store the first time stamp information in association with said first event information.

80. The system of claim 13, wherein said output indicator is configured to indicate a low battery condition of the device.

81. The system of claim 13, wherein said output indicator is visual, and said output indicator is selected from the group consisting of single monochromatic LEDs, multiple colored lights, and liquid crystal displays.

82. The system of claim 13, wherein said movement data stored in the memory is configured to be downloaded to the computer.

83. The system of claim 82, wherein the portable, self-contained movement measuring device further comprises:
software configured to communicate with the program running on the computer, wherein the program is configured to present the downloaded movement data to the user.

84. The system of claim 83, wherein said downloaded movement data is configured to be analyzed by said user via said program.

85. The system of claim 83, wherein said program is configured to interpret said movement data and produce at least one report.

86. The system of claim 83, wherein said program is configured to interpret said movement data and produce at least one history report.

87. The system of claim 86, wherein said at least one history report includes dates and times of said movement data.

88. The system of claim 83, wherein said program is configured to allow the user to program additional reports and histories with respect to said movement data of said user.

89. The system of claim 82, wherein said movement data is configured to be downloaded to said computer, using the download device, via a wired connection.

90. The system of claim 82, wherein said movement data is configured to be downloaded to said computer, using the download device, via a wireless connection.

91. The system of claim 76, wherein the output indicator is configured to provide a visual indicator to the user regarding the predetermined threshold being reached.

92. The system of claim 13, wherein the memory is configured to store the user-defined operational parameters, the user-defined operational parameters comprising a plurality of thresholds respectively corresponding to a plurality of notifications, wherein each time the movement data reaches one of the plurality of the thresholds, the microprocessor is configured to detect that one of a plurality of user-defined events occurred.

93. The system of claim 92, wherein when the microprocessor detects that one of the user-defined events occurred based on the movement data reaching one of the plurality of the thresholds, the output indicator displays a corresponding one of the notifications indicating that one of the user-defined events has occurred.

94. The system of claim 92, wherein the plurality of thresholds are different from each other.

95. The system of claim 92, wherein the plurality of notifications are different visual indicators.

96. The system of claim 95, wherein at least one of the visual indicators includes a blinking indicator.

97. The system of claim 13, wherein said output indicator is configured to signal the occurrence of user-defined events.

98. The system of claim 76, wherein said microprocessor is configured to detect occurrence of the first user-defined event by comparing said movement data to said predetermined threshold.

99. The system of claim 13, wherein said device is configured to be placed on said user's arm to monitor and record said movement data.

100. The system of claim 99, wherein said movement sensor configured to measure movement of said user's arm.

101. The system of claim 13, wherein said movement sensor configured to measure a walking distance.

102. The system of claim 101, wherein said device is configured to be wearable by the user, and said movement sensor is configured to measure said walking distance of said user.

103. The system of claim 13, wherein said microprocessor is configured to store, in said memory, date information associated with the first time stamp information,
wherein said movement sensor is configured to continuously check for said movement,
wherein said output indicator is configured to display information signaling the occurrence of the first user-defined event based on the detection of the first user-defined event and the first time stamp information,
wherein said movement data stored in the memory is configured to be downloaded to the computer,
wherein the device further comprises software configured to communicate with the program which presents the downloaded movement data,
wherein said program is configured to produce at least one report based on said movement data,
wherein the memory is configured to store the user-defined operational parameters, the user-defined operational parameters comprising a plurality of thresholds respectively corresponding to a plurality of notifications, wherein each time the movement data reaches one of the plurality of the thresholds, the microprocessor is configured to detect that one of the user-defined events occurred,
wherein said device is configured to be placed on said user's arm to monitor and record said movement data,
wherein said movement sensor configured to measure movement of said user's arm.

104. The method of claim 20, further comprising:
storing, in said memory, date information associated with the first time stamp information.

105. The method of claim 20, further comprising:
retrieving said first time stamp information from said real-time clock and associate the retrieved first time stamp information with said first user-defined event.

106. The method of claim 105, further comprising:
retrieving said first time stamp information from said real-time clock based on the detection of the first user-defined event.

107. The method of claim 20, wherein said storing comprises continuously storing said movement data after battery power is lost from a power source of the portable, self-contained movement measuring device.

108. The method of claim 20, further comprising:
continuously monitoring for said physical movement using a movement sensor of the portable, self-contained movement measuring device.

109. The method of claim 108, wherein said interpreting comprises:
continuously interpreting, based on the user-defined operational parameters, said physical movement data.

110. The method of claim 20, further comprising:
displaying, using an output indicator of the portable, self-contained movement measuring device, information signaling the occurrence of the first user-defined event based on the detection of the user-defined event.

111. The method of claim 110, wherein said output indicator displays said information signaling the occurrence of the first user-defined event based on said first time stamp information.

112. The method of claim 20, further comprising:
displaying, using an output indicator included the portable, self-contained movement measuring device, information signaling the occurrence of the first user-defined event based on the detection of the first user-defined event and the first time stamp information.

113. The method of claim 20, wherein said at least one of the user-defined operational parameters is a predetermined threshold, and said first user-defined event occurs when the movement data reaches the predetermined threshold.

114. The method of claim 113, wherein an output indicator of the portable, self-contained movement measuring device displays information signaling the occurrence of the first user-defined event when the movement data reaches the predetermined threshold.

115. The method of claim 113, further comprising:
storing, in said memory, said first event information indicating that the predetermined threshold is met.

116. The method of claim 115, further comprising:
storing, in said memory, the first time stamp information in association with said first event information.

117. The method of claim 20, further comprising:
indicating a low battery condition, using an output indicator of the portable, self-contained movement measuring device.

118. The method of claim 20, wherein said physical movement data stored in the memory is the interpreted physical movement data, and said stored physical movement data is configured to be downloaded to a computer.

119. The method of claim 118, further comprising:
communicating with external software, wherein the external software is configured to present said interpreted physical movement data to the user.

120. The method of claim 119, wherein said external software is configured to run on a computer.

121. The method of 20, further comprising:
producing a report based on said interpreted physical movement data.

122. The method of 119, further comprising:
producing at least one report based on said interpreted physical movement data using the external software.

123. The method of claim 119, further comprising:
producing at least one history report based on said interpreted physical movement data using the external software.

124. The method of claim 123, wherein said at least one history report includes dates and times of said physical movement data.

125. The method of claim 119, further comprising:
providing additional reports and histories with respect to said interpreted physical movement data, wherein the additional reports and histories are programmed by the user via the external software.

126. The method of claim 118, wherein said physical movement data is configured to be downloaded to said computer via a wired connection.

127. The method of claim 118, wherein said movement data is configured to be downloaded to the computer via a wireless connection.

128. The method of claim 113, further comprising:
providing, via an output indicator of the portable, self-contained movement measuring device, a visual indicator to the user regarding the predetermined threshold being reached.

129. The method of claim 20, further comprising:
storing the user-defined operational parameters, the user-defined operational parameters comprising a plurality of thresholds respectively corresponding to a plurality of notifications, wherein the detecting comprises detecting occurrence of one of a plurality of user-defined events each time the movement data reaches one of the plurality of the thresholds.

130. The method of claim 129, wherein in response to detecting that one of the user-defined events occurred based on the movement data reaching one of the plurality of the thresholds, the method further comprises:
displaying, via an output indicator of the portable, self-contained movement measuring device, a corresponding one of the notifications indicating that one of the user-defined events has occurred.

131. The method of claim 129, wherein the plurality of thresholds are different from each other.

132. The method of claim 129, wherein the plurality of notifications are different visual indicators.

133. The method of claim 132, wherein at least one of the visual indicators includes a blinking indicator.

134. The method of claim 20, further comprising:
signaling, using an output indicator included in the portable, self-contained movement measuring device, the occurrence of user-defined events.

135. The method of claim 113, wherein the detecting comprises comparing said physical movement data to said predetermined threshold.

136. The method of claim 20, wherein said body part is a user's arm, and said measuring the data comprises monitoring and recording the physical movement of said user's arm.

137. The method of claim 136, wherein said measuring the data comprises measuring the data using a movement sensor of the portable, self-contained movement measuring device.

138. The method of claim 20, further comprising:
measuring a walking distance based on the interpreted physical movement data.

139. The method of claim 20, further comprising:
storing, in said memory, date information associated with the first time stamp information;
continuously monitoring for said physical movement using a movement sensor of the portable, self-contained movement measuring device;
displaying, using an output indicator included the portable, self-contained movement measuring device, information signaling the occurrence of the first user-defined event based on the detection of the first user-defined event and the first time stamp information,
wherein said physical movement data stored in the memory is the interpreted physical movement data, and said stored physical movement data is configured to be downloaded to a computer;
communicating with external software configured to run on the computer and present said interpreted physical movement data to the user;
producing a report based on said interpreted physical movement data using the external software; and
storing the user-defined operational parameters, the user-defined operational parameters comprising a plurality of thresholds respectively corresponding to a plurality of notifications, wherein the detecting comprises detecting occurrence of one of a plurality of user-defined events each time the movement data reaches one of the plurality of the thresholds,
wherein said body part is a user's arm, and said measuring the data comprises monitoring and recording the physical movement of said user's arm.

140. The device of claim 1, wherein the user-defined operational parameters comprise a first predetermined threshold and a second predetermined threshold different from the first predetermined threshold,
wherein the first user-defined event occurs when the movement data reaches the first predetermined threshold and a second user-defined event occurs when the movement data reaches the second predetermined threshold,
wherein said microprocessor is configured to interpret said movement data to determine whether the movement data reaches the first predetermined threshold and whether the movement data reaches the second predetermined threshold.

141. The device of claim 140, wherein the output indicator is configured to display first information indicating occurrence of the first user-defined event when it is determined that the first predetermined threshold is met, and configured to display second information indicating occurrence of the second user-defined event when it is determined that the second predetermined threshold is met.

142. The device of claim 141, wherein the displayed first information is different from the displayed second information.

143. The device of claim 1, wherein the first user-defined event is a movement exceeding a user-defined angle limit and the first time stamp information reflects a time at which the movement exceeded the user-defined angle limit.

144. The device of claim 1, wherein said first user-defined event is a predetermined type of movement.

145. The device of claim 144, wherein the predetermined type of movement is movement exceeding a predetermined angle limit.

146. The device of claim 144, wherein the predetermined type of movement is movement exceeding a predefined speed.

147. The device of claim 144, wherein the predetermined type of movement is no movement for a predetermined amount of time.

148. The device of claim 144, wherein the predetermined type of movement is a maximum number of incorrect movements allowed in a predetermined time period.

149. The device of claim 1, wherein said microprocessor is configured to detect a second event based on the movement data and at least one of the user-defined operational parameters, and said microprocessor is configured to store, in said memory, second event information related to the detected second event along with second time stamp information reflecting a time at which the movement data causing the second event occurred.

150. The device of claim 149, wherein said second event is a predetermined type of movement.

151. The device of claim 150, wherein the predetermined type of movement is movement exceeding a predetermined angle limit.

152. The device of claim 150, wherein the predetermined type of movement is movement exceeding a predefined speed.

153. The device of claim 150, wherein the predetermined type of movement is no movement for a predetermined amount of time.

154. The device of claim 150, wherein the predetermined type of movement is a maximum number of incorrect movements allowed in a predetermined time period.

155. The system of claim 13, wherein the user-defined operational parameters comprise a first predetermined threshold and a second predetermined threshold different from the first predetermined threshold,
wherein the first user-defined event occurs when the movement data reaches the first predetermined threshold and a second user-defined event occurs when the movement data reaches the second predetermined threshold,
wherein said microprocessor is configured to interpret said movement data to determine whether the movement data reaches the first predetermined threshold and whether the movement data reaches the second predetermined threshold.

156. The system of claim 155, wherein the output indicator is configured to display first information indicating occurrence of the first user-defined event when it is determined that the first predetermined threshold is met, and configured to display second information indicating occurrence of the second user-defined event when it is determined that the second predetermined threshold is met.

157. The system of claim 156, wherein the displayed first information is different from the displayed second information.

158. The system of claim 13, wherein the first user-defined event is a movement exceeding a user-defined angle limit and the first time stamp information reflects a time at which the movement exceeded the user-defined angle limit.

159. The system of claim 13, wherein said first user-defined event is a predetermined type of movement.

160. The system of claim 159, wherein the predetermined type of movement is movement exceeding a predetermined angle limit.

161. The system of claim 159, wherein the predetermined type of movement is movement exceeding a predefined speed.

162. The system of claim 159, wherein the predetermined type of movement is no movement for a predetermined amount of time.

163. The system of claim 159, wherein the predetermined type of movement is a maximum number of incorrect movements allowed in a predetermined time period.

164. The system of claim 13, wherein said microprocessor is configured to detect a second event based on the movement data and at least one of the user-defined operational parameters, and said microprocessor is configured to store, in said memory, second event information related to the detected second event along with second time stamp information reflecting a time at which the movement data causing the second event occurred.

165. The system of claim 164, wherein said second event is a predetermined type of movement.

166. The system of claim 165, wherein the predetermined type of movement is movement exceeding a predetermined angle limit.

167. The system of claim 165, wherein the predetermined type of movement is movement exceeding a predefined speed.

168. The system of claim 165, wherein the predetermined type of movement is no movement for a predetermined amount of time.

169. The system of claim 165, wherein the predetermined type of movement is a maximum number of incorrect movements allowed in a predetermined time period.

170. The system of claim 13, wherein said movement sensor comprises at least one accelerometer.

171. The method of claim 20, wherein the user-defined operational parameters comprise a first predetermined threshold and a second predetermined threshold different from the first predetermined threshold, wherein the first user-defined event occurs when the movement data reaches the first predetermined threshold and a second user-defined event occurs when the movement data reaches the second predetermined threshold, wherein said interpreting comprises interpreting said movement data to determine whether the movement data reaches the first predetermined threshold and whether the movement data reaches the second predetermined threshold.

172. The method of claim 171, further comprising:

displaying, using an output indicator included in the portable, self-contained movement measuring device, first information indicating occurrence of the first user-defined event when it is determined that the first predetermined threshold is met and second information indicating occurrence of the second user-defined event when it is determined that the second predetermined threshold is met.

173. The method of claim 172, wherein the displayed first information is different from the displayed second information.

174. The method of claim 20, wherein the first user-defined event is a movement exceeding a user-defined angle limit and the first time stamp information reflects a time at which the movement exceeded the user-defined angle limit.

175. The method of claim 20, wherein said first user-defined event is a predetermined type of movement.

176. The method of claim 175, wherein the predetermined type of movement is movement exceeding a predetermined angle limit.

177. The method of claim 175, wherein the predetermined type of movement is movement exceeding a predefined speed.

178. The method of claim 175, wherein the predetermined type of movement is no movement for a predetermined amount of time.

179. The method of claim 175, wherein the predetermined type of movement is a maximum number of incorrect movements allowed in a predetermined time period.

180. The method of claim 20, further comprising:

detecting, using the microprocessor, a second event based on the movement data and at least one of the user-defined operational parameters; and storing, in said memory, second event information related to the detected second event along with second time stamp information reflecting a time at which the movement data causing the second event occurred.

181. The method of claim 180, wherein said second event is a predetermined type of movement.

182. The method of claim 181, wherein the predetermined type of movement is movement exceeding a predetermined angle limit.

183. The method of claim 181, wherein the predetermined type of movement is movement exceeding a predefined speed.

184. The method of claim 181, wherein the predetermined type of movement is no movement for a predetermined amount of time.

185. The method of claim 181, wherein the predetermined type of movement is a maximum number of incorrect movements allowed in a predetermined time period.

* * * * *